United States Patent
Lee (10) Patent No.: US 9,034,820 B2
(45) Date of Patent: May 19, 2015

(54) METHOD AND COMPOSITION FOR MODULATING ERYTHROPOIESIS

(76) Inventor: Hsinyu Lee, San Diego, CA (US)

( * ) Notice: Subject to any disclaimer, the term of this patent is extended or adjusted under 35 U.S.C. 154(b) by 0 days.

(21) Appl. No.: 13/419,405

(22) Filed: Mar. 13, 2012

(65) Prior Publication Data

US 2012/0270780 A1 Oct. 25, 2012

Related U.S. Application Data (60) Provisional application No. 61/464,987, filed on Mar. 14, 2011.

(51) Int. Cl.
| | |
|---|---|
| *A61K 38/18* | (2006.01) |
| *A61K 31/42* | (2006.01) |
| *C07D 261/02* | (2006.01) |
| *C07F 9/10* | (2006.01) |
| *C07F 9/38* | (2006.01) |

(52) U.S. Cl.
CPC .............. *C07D 261/02* (2013.01); *C07F 9/10* (2013.01); *C07F 9/103* (2013.01); *C07F 9/3808* (2013.01)

(58) Field of Classification Search
None
See application file for complete search history.

(56) References Cited

U.S. PATENT DOCUMENTS

| | | | |
|---|---|---|---|
| 5,565,439 | A | 10/1996 | Piazza et al. |
| 6,004,579 | A | 12/1999 | Bathurst et al. |
| 6,380,177 | B1 | 4/2002 | Erickson |
| 6,949,529 | B2 | 9/2005 | Bathurst et al. |
| 7,169,818 | B2 | 1/2007 | Lynch et al. |
| 7,217,704 | B2 | 5/2007 | Miller et al. |
| 2003/0027800 | A1 | 2/2003 | Miller et al. |
| 2005/0042687 | A1* | 2/2005 | Kelly et al. ............ 435/7.2 |
| 2006/0009507 | A1 | 1/2006 | Miller et al. |
| 2008/0051372 | A1 | 2/2008 | Chun |

OTHER PUBLICATIONS

Signal transduction in erythropoiesis. Mason-Garcia M, Beckman BS. FASEB J. Nov. 1991;5(14):2958-64.*
Blood. Apr. 1, 2000;95(7):2420-5. Lysophosphatidic acid opens a Ca(++) channel in human erythrocytes. Yang L, Andrews DA, Low PS.*
Identification of a phosphothionate analogue of lysophosphatidic acid (LPA) as a selective agonist of the LPA3 receptor. Hasegawa Y, Erickson JR, Goddard GJ, Yu S, Liu S, Cheng KW, Eder A, Bandoh K, Aoki J, Jarosz R, Schrier AD, Lynch KR, Mills GB, Fang X. J Biol Chem. Apr. 4, 2003;278(14):11962-9. Epub Jan. 27, 2003.*
Stem cell regulation by lysophospholipids. Pébay A, Bonder CS, Pitson SM. Prostaglandins Other Lipid Mediat. Nov. 2007;84(3-4):83-97. Epub Sep. 5, 2007.*
Lysophosphatidic acid induces erythropoiesis through activating lysophosphatidic acid receptor 3. Chiang CL, Chen SS, Lee SJ, Tsao KC, Chu PL, Wen CH, Hwang SM, Yao CL, Lee H. Stem Cells. Nov. 2011;29(11):1763-73. doi: 10.1002/stem.733.*
High red blood cell count Mayo Clinic staff http://www.mayoclinic.com/health/high-red-blood-cell-count/MY00111.*
Animal Models of Disease Ma C. Modern Drug Discovery. Jun. 2004; 7(6): 30-36.*
Clin Lipidol. Aug. 2011;6(4):413-426. Lysophosphatidic acid effects on atherosclerosis and thrombosis. Cui MZ.*
The therapeutic potential of erythropoiesis-stimulating agents for tissue protection: a tale of two receptors. Brines M. Blood Purif. 2010;29(2):86-92. Epub Jan. 8, 2010.*
Moritz et al (Am J Physiol. Dec. 1997;273(6 Pt 2):R1829-44).*
Ye XQ, Hama K, Contos JJA, et al. LPA(3)-mediated lysophosphatidic acid signalling in embryo implantation and spacing. Nature. 2005;435(7038):104-108.
Lai JM, Lu CY, Yang-Yen HF, Chang ZF. Lysophosphatidic acid promotes phorbol-ester-induced apoptosis in TF-1 cells by interfering with adhesion. Biochemical Journal. 2001; 359:227-233.
Bagga S, Price KS, Lin DA, Friend DS, Austen KF, Boyce JA. Lysophosphatidic acid accelerates the development of human mast cells. Blood. 2004;104(13):4080-4087.
Hama K. and Aoki J., LPA3, a unique G protein-coupled receptor for lysophosphatidic acid. Progress in Lipid Research 49:335-342 (2010).
Aoki J., Inoue A. and Okudaira S., Two pathways for lysophosphatidic acid production. Biochim. Biophys. Acta, 1781: 513-518 (2008).
Lin et al. (1985) Proc. Natl. Acad. Sci. USA 82:7580-7584.
Bandoh et al., Molecular cloning and characterization of a novel human G-protein-coupled receptor, EDG7, for lysophosphatidic acid. J. Biol. Chem. 274 (39): 27776-85, Sep. 1999.
Tamaruya Y. et al., Angew. Chem. (Int. Ed. Engl.) 43: 2834 (2004).
Heise C.E. et al., Mol. Pharmacol. 60: 1173, (2001).
Xu Y. et al., J. Med. Chem. 48: 3319-3327 (2005).
Kano K., et al., LPA and its analogs- attractive tools for elucidation of LPA biology and drug development. Curr. Med. Chem. 15: 2122-2131 (2008).
Noguchi K., et al., Lysophosphate acid (LPA) and its receptors. Curr. Opin. Pharmacol. 9: 15-23 (2009).

* cited by examiner

*Primary Examiner* — Brian J Gangle
*Assistant Examiner* — Andrea McCollum
(74) *Attorney, Agent, or Firm* — Chang-Hsing Liang (57) ABSTRACT

The invention generally relates to compositions and methods of their use. More specifically, the invention relates to the use of a compound in modulating erythropoiesis in a subject by mediating the activity and/or quantity of a member present in the $LPA_3$-mediated signaling pathway, such as lysophosphatidic acid receptor subtype 3 ($LPA_3$).

13 Claims, 7 Drawing Sheets

METHOD AND COMPOSITION FOR MODULATING ERYTHROPOIESIS

CROSS-REFERENCE TO RELATED APPLICATIONS

The present invention claims priority to U.S. provisional application Ser. No. 61/464,987 filed Mar. 14, 2011, the entirety of which is hereby incorporated by reference.

FIELD OF THE INVENTION

The invention generally relates to pharmaceutical compositions and methods of their use. More specifically, the invention relates to pharmaceutical compositions comprising a compound that activates lysophosphatidic acid receptor subtype 3 ($LPA_3$) to be used to elicit erythropoiesis in a subject.

DESCRIPTION OF THE RELATED ART

Erythropoiesis, one of the main processes of hematopoiesis, depends on the unique ability of hematopoietic stem cells (HSCs) to proliferate and differentiate into progenitors of red blood cells. Recently, $CD34^+$ stem cells derived from umbilical cord blood have provided a promising alternative to bone marrow for differentiation research. In the multi-step process of erythropoiesis, HSCs can be induced into progenitor cells and erythroblasts and terminally differentiate into red blood cells with nuclear condensation and extrusion. The expansion and differentiation of HSCs were reported in liquid culture using a variety of recombinant human cytokine combinations with stem cell factor (SCF) and erythropoietin. (EPO), which play essential roles in erythropoiesis. Several signaling pathways are known to regulate hematopoiesis and erythropoiesis. The binding of EPO and its receptor (EPOR) activates c-Jun-activated kinase (JAK), which stimulates intracellular pathways such as, Ras/mitogen-activated protein (MAP) kinase, phosphatidylinositol 3-kinase (PI3K), and signal transducer and activator of transcription (STAT) transcription factors, to regulate erythroid differentiation and survival. GATA-1 is an essential transcription factor modulated by the EPOR/PI3-kinase/AKT pathway and it mediate specific target genes influencing the development of an erythroid progenitor in apoptosis, proliferation, and terminal differentiation.

Lysophosphatidic acid (LPA) is a simple phospholipid mediator which stimulates cell proliferation, migration, and survival of multiple cell types. LPA receptors, formerly designated EDG receptors, are GPCRs and widely exist in tissues and exert diverse bioactivities. To date, up to five LPA receptors were identified. Among these receptors, $LPA_1$, $LPA_2$, and $LPA_3$ are widely expressed in most tissues and react with $G_i$, $G_q$, $G_{12/13}$, or Gs.[13] $LPA_4$ is expressed in specific organs, such as the pancreas, ovaries, and thymus; it raises intracellular $Ca^{2+}$ and cAMP levels through activating $G_q$ and $G_{12/13}$. $LPA_5$, expressed at low levels in multiple tissues, reacts with Gq and $G_{12/13}$ and increases intracellular cAMP levels. The specific functions of each receptor were elucidated by studies using LPA receptor gene-deficient mice. $LPA_1$-deficient mice exhibited reduced suckling, attributed to olfactory defects, and developmental abnormalities in the neurological system, whereas $LPA_2$ knockouts had no obvious phenotype. In addition, $LPA_3$-knockout mice had delayed uterine implantation, altered embryo spacing, and reduced litter sizes (Ye X Q, Hama K, Contos J J A, et al. LPA(3)-mediated lysophosphatidic acid signalling in embryo implantation and spacing. *Nature.* 2005; 435(7038):104-108.). $LPA_4$ deletion did not display a noticeable phenotype. However, embryonic fibroblasts from $LPA_4$-knockout mouse responded with hypersensitivity to LPA-induced cell migration. Recent studies also showed that stem cell differentiation is regulated through LPARs. LPA accelerates proliferation and differentiation of human mast cells derived from cord blood through LPARs and PPARγ-dependent pathways. In addition, LPA induces osteoblastic differentiation from TERT-overexpressed human mesenchymal stem cells (hMSCs-TERT) through an interplay of LPA1 and LPA4. However, the roles of LPA during the erythropoiesis process remain unclear.

Lysophospholipids, including LPA and sphingosine 1-phosphate (S1P), were recently demonstrated to be regulators of cell fate determination in a variety of stem cells and their progenitors. LPA and S1P were shown to modulate proliferation, survival, differentiation, and migration of embryonic and neural stem cells. In mouse hematopoietic progenitors, $LPA_1$, $LPA_2$, and $S1P_{1-4}$, but not $LPA_3$ or $S1P_5$, were expressed in primitive Lin-$Sca^+$ $Kit^+$ cells isolated from bone marrow. In addition, LPA and S1P enhanced the chemotactic response in primitive HSCs stimulated by stromal-derived factor (SDF)-1. In human hematopoietic progenitor cells, only a few studies demonstrated the effects of LPA. LPA inhibits cell adhesion of the TF-1 erythroblastic progenitor cell line through a Rho-dependent pathway presumably via $G_{12/13}$. However, the actual receptors involved were not determined (Lai J M, Lu C Y, Yang-Yen H F, Chang Z F. Lysophosphatidic acid promotes phorbol-ester-induced apoptosis in TF-1 cells by interfering with adhesion. *Biochemical Journal.* 2001; 359:227-233.). Furthermore, LPA stimulation accelerated the development of cord blood-derived cultured to human mast cells (hMCs) in vitro. The stimulation was mediated through LPA-receptor and PPARγ-dependent pathways to enhance hMC proliferation and differentiation (Bagga S, Price K S, Lin D A, Friend D S, Austen K F, Boyce J A. Lysophosphatidic acid accelerates the development of human mast cells. *Blood.* 2004; 104(13):4080-4087.). In addition, LPA was also reported to enhance osteogenic differentiation of human mesenchymal stem cells (hMSCs-TERT). LPA-induced osteogenic differentiation is controlled by the interplay between $LPA_1$ and $LPA_4$: activation of $LPA_1$ leads to an increase in intracellular $Ca^{2+}$ and induces osteogenesis, whereas activation of $LPA_4$ results in increased cAMP production and inhibits osteogenic differentiation. The mechanisms of LPA's regulation of stem cell differentiation remain unclear, especially in HSCs.

Erythropoietin (EPO) is a glycoprotein produced naturally in very low levels by the kidneys. It has been produced on a commercial scale using recombinant DNA technology and used clinically to elicit formation of red blood cells in bone marrow. However, it has been reported that EPO could cost roughly USD$8,000 per anemia patient every year (*Science* 251(4998), pp. 1158-1159), indicating that the EPO treatment is so expensive as to cause a tremendous economic burden on the health care system of every country.

Thus, there is a need for substantially non-toxic compositions and methods that can restore or maintain the production of red blood cells at a normal level. In particular, there is an increasing need for methods and compositions to reduce the amount of erythropoietin used in the treatment of anemia and hypoxia.

SUMMARY OF THE INVENTION

The inventors surprisingly found that LPA enhances an EPO-dependent erythropoietic process through activating $LPA_3$ activity and that the specific blockage of $LPA_3$ signaling inhibits the LPA-enhanced erythropoietic process, and from there devise a novel treatment for disorders or conditions associated with an abnormal level of red blood cells, such as anemia, erythroid hyperplasia, and the diseases or conditions associated therewith. Such diseases and conditions include those described below.

According to the first aspect of the invention, it is to provide a method for modulating erythropoiesis in a subject comprising administering to said subject a compound capable of modulating the activity of LPA receptor subtype 3 ($LPA_3$) pathway.

According to the second aspect of the invention, it is to provide a pharmaceutical composition for modulating erythropoiesis, comprising a compound capable of modulating the activity of $LPA_3$ pathway.

The third aspect of the invention relates to use of a compound capable of modulating the activity of $LPA_3$ pathway for the manufacture of a medicament for modulating erythropoiesis in a subject.

The fourth aspect of the invention relates to a method for treating or preventing a disorder or a condition associated with an abnormal level of red blood cells in a subject, comprising administering to said subject a compound capable of modulating the activity of $LPA_3$ pathway.

The fifth aspect of the invention relates to use of a compound capable of modulating the activity of $LPA_3$ pathway for the manufacture of a medicament for treating or preventing a disorder or a condition associated with an abnormal level of red blood cells in a subject.

The sixth aspect of the invention relates to a pharmaceutical composition for treating or preventing a disorder or a condition associated with an abnormal level of red blood cells in a subject, comprising a compound capable of modulating the activity of $LPA_3$ pathway.

BRIEF DESCRIPTION OF THE DRAWINGS

The above and other objects, features and effects of the invention will become apparent with reference to the following description of the preferred embodiments taken in conjunction with the accompanying drawings, in which:

FIGS. 1(A) and (B) are diagrams illustrating hematopoietic defects in $zLPA_3$-knockdown zebrafish, in which FIG. 1(A) shows hematopoiesis defects classified into normal, moderate and severe based on the amounts of red blood cells measured by o-dianisidine staining; and FIG. 1(B) shows dose-dependent effects of $zLPA_3$ tMO1 and tMO2;

FIGS. 2(A) and (B) are diagrams illustrating In vitro hematopoiesis using human $CD133^+$ hemopoietic stem cells (hHSCs), in which FIG. 2(A) shows that hHSCs underwent both proliferation and differentiation in four stages and the progenitor cell number expanded by 30-, 20-, and 10-fold; and FIG. 2(B) shows expression patterns of $LPA_1$ (black) and $LPA_3$ (gray) during different stages;

FIGS. 3(A) and (B) are diagrams demonstrating erythropoietic inhibition caused by Ki16425, in which FIG. 3(A) shows mRNA expressions of CD71 and GlyA in hHSCs harvested from stages II (black) and III (gray) as measured by a real-time PCR; and FIG. 3(B) shows that cells treated with the DMSO control (i), Ki treatment in stage II (ii), stage III (iii) and continually in stages II and III (iv) were stained with CD71 and GlyA monoclonal antibodies;

FIGS. 4(A), (B) and (C) LPA are diagrams illustrating receptors knockdown in erythropoietic processes, wherein FIG. 4(A) shows the knockdown efficacy of $LPA_1$ and $LPA_3$ shRNA; FIG. 4(B) shows mRNA levels of CD71 and GlyA in $LPA_1$- and $LPA_3$-knockdown cells in stages II (black) and III (gray); and FIG. 4(C) shows the CD71 and GlyA expressions of $LPA_1$- and $LPA_3$-knockdown cells as analyzed by flow cytometry in stage III;

FIGS. 5(A) and (B) are diagrams demonstrating enhancement of erythrocyte differentiation by LPA treatment, in which FIG. 5(A) shows that, in stage II, a 24-hour of LPA treatment elevated mRNA levels of CD71, GlyA and GATA-1 in concentration-dependent manners; and FIG. 5(B) show an increase in CD71 protein levels at the end of stage II induction;

FIGS. 7(A) and (B) are diagrams demonstrating the suppression of LPA-enhanced differentiation by quercetin, in which FIG. 7(A) shows that the CD71 mRNA level increased with culture with LPA, but was inhibited by quercetin and Ki16425 treatment; and FIG. 7(B) shows that at the end of stage II induction, the enhancement of CD71 protein level was suppressed by quercetin (20 μM).

DETAILED DESCRIPTION OF THE INVENTION

In the in vivo study described below, the inventors used an antisense $zLPA_3$-morpholino oligonucleotide (MO) to knock down $LPA_3$ in zebrafish, and hemopoietic defects were observed in injected embryos. Furthermore, the inventors cultured cord blood-derived human (h)HSCs in vitro and detected that $LPA_1$ and $LPA_3$ were expressed in the progenitor and erythroblast stages. Erythropoietic differentiation was abolished by Ki16425, a pharmacological blocker of $LPA_1$ and $LPA_3$, as evaluated by mRNA and protein expressions of CD71 and GlyA. Furthermore, using electrical nucleofection, we found that knockdown of $LPA_3$, but not of $LPA_1$, specifically inhibited the erythropoietic process. In addition, LPA also induced the expression of these erythroid biomarkers in cultured hHSCs under plasma-free conditions. Translocation of β-catenin into the nucleus, a downstream response of LPA receptor activation, was blocked by Ki16425 treatment. Furthermore, quercetin, an inhibitor of the β-catenin/TCF pathway, blocked LPA-enhanced hematopoiesis. In conclusion, our study indicated that LPA induced an EPO-dependent erythropoietic process through activating $LPA_3$, and β-catenin translocation may participate in this process. The invention thus provides a novel method for modulating erythropoiesis.

According to the invention, it is found for the first time that the $LPA_3$-mediated signaling pathway controllingly influences the erythropoietic process, suggesting that regulating the activity and/or quantity of the members present in the $LPA_3$-mediated signaling pathway in a subject that possesses the signaling pathway would lead to a change in erythropoiesis in said subject. The members in the $LPA_3$-mediated signaling pathway encompass bio-molecules that involve in the biosynthesis and biodegradation of ligands of $LPA_3$ and the ligands thus synthesized, such as LPA and the enzymes and intermediates for LPA synthesis or degradation, or in the signal transducing cascade of $LPA_3$, such as $LPA_3$ itself and its downstream effectors including, for example, β-catenin. Examples of the members include those described in Hama K. and Aoki J., $LPA_3$, a unique G protein-coupled receptor for lysophosphatidic acid. *Progress in Lipid Research* 49:335-342 (2010); and Aoki J., Inoue A. and Okudaira S., Two pathways for lysophosphatidic acid production. *Biochim. Biophys. Acta,* 1781: 513-518 (2008). One with ordinary skill in the art will understand that any of the members in said signaling pathway, either known in the art or to be identified, is within the scope of the invention, so long as it contributes to enhancement, stimulation or inhibition of the erythropoietic process. Thus, the object of modulating erythropoiesis in the subject can be achieved by bringing a member of the LPA$_3$ signaling pathway in contact with a compound capable of modulating the activity of the member.

In some embodiments, the invention provides a method for modulating erythropoiesis in a subject comprising administering to said subject a compound capable of modulating the activity of LPA$_3$ signaling pathway.

The term "erythropoiesis" is used herein to describe the process of proliferation and differentiation of hematopoietic stem cells (HSCs) and hematopoietic progenitor cells, leading to the production of mature red blood cells. In some embodiments, the erythropoiesis is directed to an "erythropoietin-dependent erythropoiesis," which refers to the erythropoietic process regulated and promoted by erythropoietin. According to the invention, "modulating erythropoiesis" as used herein refers to enhancing, stimulating or inhibiting the erythropoietic process, especially the EPO-dependent erythropoiesis. More specifically, "modulating erythropoiesis" means that the composition and method of the invention alter the quantity of hematopoietic progenitor cells proliferated and differentiated into mature red blood cells, so that the quantity of the mature and functional red blood cells in blood is restored to a normal level necessary for oxygen transport in a healthy subject.

As used herein, the term "erythropoietin," or abbreviated as "EPO," is intended to encompass naturally occurring and recombinant species thereof, as well as functionally equivalent variants or fragments thereof, including human erythropoietin (GENBANK® Accession No. AAA52400; Lin et al. (1985) *Proc. Natl. Acad. Sci. USA* 82:7580-7584), commercially available EPOETIN products under the trade names of Epogen® (Amgen, Inc., Thousand Oaks, Calif.), Eprex® (Janssen-Cilag. Ortho Biologics LLC) and NeoRecormon® (Roche), ARANESP human recombinant erythropoietin (Amgen) and PROCRIT® (Ortho Biotech Products, L.P., Raritan N.J.).

As used herein, the term "lysophosphatidic acid," or abbreviated as "LPA," refers to the compound having an IUPAC name of (2-hydroxy-3-phosphonooxypropyl) (Z)-octadec-9-enoate, which is known to be capable of binding to and activating G-protein-coupled receptors including LPA$_1$, LPA$_2$ and LPA$_3$ (also known as EDG2, EDG4, and EDG7), and LPA$_4$ (p2y9/GPR23) and LPA$_5$ (GPR92).

The term "LPA receptor subtype 3," or abbreviated as "LPA$_3$," refers to the cellular receptor which was found to interact with LPA and other lysophospholipids to manifest physiological or pathophysiological effects of LPA (Bandoh et al., Molecular cloning and characterization of a novel human G-protein-coupled receptor, EDG7, for lysophosphatidic acid. *J. Biol. Chem.* 274 (39): 27776-85, September, 1999). Human LPA$_3$ has a nucleotide sequence deposited in the GenBank database with the Accession No. NM-012152.

The term "compound capable of modulating the activity of LPA$_3$ signaling pathway" is intended to encompass those capable of modulating the activity of a member of the LPA$_3$ signaling pathway to consequently result in enhancement, stimulation or inhibition of the erythropoietic process. In a preferred embodiment, the compound is one capable of mediating the receptor activity of LPA$_3$. In another embodiment, the compound is one capable of modulating the translocation of β-catenin into nuclei. In still another embodiment, the compound is one capable of modulating the enzymatic activity of an enzyme for synthesizing LPA, such as autotoxin (ATX).

The terms "compound capable of mediating the activity of LPA$_3$," and "LPA$_3$-mediating compound" are interchangeably used herein to refer to compounds that bind to LPA$_3$ to induce a detectable increase or decrease in receptor activity in vivo and in vitro (for example, at least a 10% increase or decrease in receptor activity). The compounds include, but are not limited to, LPA, LPA analogs, LPA derivatives, LPA precursors and metabolites, LPA$_3$ agonists and antagonists, and other agents, which, either known in the art or to be developed, are sufficiently structurally similar to LPA to elicit or suppress the biological pathways mediated by LPA$_3$. Some of the LPA analogs and LPA$_3$ agonists/antagonists that may be useful for the purposes of the invention are disclosed in, for example, U.S. Pat. No. 7,169,818; U.S. Pat. No. 6,949,529; U.S. Pat. No. 6,380,177; U.S. Pat. No. 6,004,579; U.S. Pat. No. 5,565,439; U.S. Pat. No. 7,217,704; US2003/0027800, US2006/0009507 and US2008/0051372, the entirety of each of which is incorporated herein by reference. It should be understood that the activity of the variant analogs, mimetics, agonists, antagonists or derivatives thereof can be less potent or more potent than LPA. Examples of these compounds include, but are not limited to, LPA$_3$ agonists, such as LPA, 2-acyl-LPA with unsaturated fatty acids (including 2-arachidonoyl-LPA), sphingosine 1-phosphate (S1P), lysophosphatidyl choline (LPC), sphingosylphosphorylcholine, 1-oleoyl-2-O-methyl-rac-glycerophosphothionate (OMPT), (3S)-1-fluoro-3-hydroxy-4-butyl-1-phosphonate (XY-17), T13 and T10 (see, for example, Tamaruya Y. et al., *Angew. Chem. (Int. Ed. Engl.)* 43: 2834 (2004)), VPC12086 and VPC31143 (see, for example, Heise C. E. et al., *Mol. Pharmacol.* 60: 1173, (2001)), mono-fluorinated analogs of LPA (Xu Y. et al., *J. Med. Chem.* 48: 3319-3327 (2005)); and LPA$_3$ antagonists, such as 3-[({4-[4-({[1-(2-chloro-4-methylphenyl)ethoxy]carbonyl}amino)-3-methyl-1,2-oxazol-5-yl]phenyl}methyl)sulfanyl]propanoic acid (Ki16425), diacylglycerol pyrophosphate (DGPP), VPC12249 (see Heise C. E. et al., supra) and dioctyl-PA; and the pharmaceutically acceptable salts thereof. These and other LPA$_3$ agonists/antagonists, as well as their chemical structures, are generally described in, for example, Kano K., et al., LPA and its analogs—attractive tools for elucidation of LPA biology and drug development. *Curr. Med. Chem.* 15: 2122-2131 (2008); Noguchi K., et al., Lysophosphate acid (LPA) and its receptors. *Curr. Opin. Pharmacol.* 9: 15-23 (2009); and Hama K. and Aoki J., *Progress in Lipid Research* 49:335-342 (2010).

In some embodiments, the LPA$_3$-mediating compound used is selective for LPA$_3$, i.e., exhibits higher binding affinity and specificity for LPA$_3$ than for the other LPA receptor subtypes. In a preferred embodiment, the compounds selective for LPA$_3$ include LPA derivatives having a phosphonate or thiophosphate group in place of the phosphate group, such as OMPT, 1-O-acyl-α-fluoromethylenephosphonate, α-hydroxymethylenephosphonate LPA analogues, and XY-17, T13 and T10. Examples of the pharmaceutically acceptable salts include, but are not limited to, salts with inorganic bases, such as sodium, potassium, magnesium and calcium and ammonium salts, and salts with organic bases, such as lysine, N,N-dibenzylethylenediamine and angelic acid. Many of the compounds are commercially available from, for example, Avanti Polar Lipids Inc. of Alabaster, Ala.

Autotoxin (ATX) is responsible for the conversion of lysophospholipids to LPA by functioning as a lysophospholipase D. In the case where the compound capable of modulating the enzymatic activity of ATX is employed, it is preferably a compound that exhibits an ATX inhibitory activity, such as ccPA, L-histidine, VPC8a202, Darmstoff analogs and thiophosphoric acid O-octadec-9-enyl ester, or an ATX enhancing activity. These compounds and their chemical structures are generally described in Kano K., et al., supra.

Alternatively, in the case where the compound capable of modulating the nuclear translocation of β-catenin is employed, it is preferably a compound that suppresses the translocation of β-catenin, such as quercetin, epigallocatechin-3-gallate (EGCG), curcumin and resveratrol, or elicits the translocation.

As used herein, the term "subject" refers to any organism in which red blood cells are utilized as principal means for delivering oxygen. Thus, the term "subject" is intended to encompass human or non-human mammal or animal. Non-human mammals include livestock animals, companion animals, laboratory animals, and non-human primates. Non-human subjects also include, without limitation, horses, cows, pigs, goats, dogs, cats, mice, rats, guinea pigs, gerbils, hamsters, mink, rabbits and fish. It is understood that the preferred subject is a human.

In some embodiments, the term "subject" refers to a biological sample as defined herein, which includes but is not limited to a cell, tissue, or organ that is isolated from an organism in which red blood cells are utilized as principal means for delivering oxygen. Accordingly, the methods, uses and compositions disclosed herein are intended to be applied in vivo as well as in vitro.

In one embodiment, the invention provides a method for treating or preventing a disorder or a condition associated with an abnormal level of red blood cells in a subject, comprising administering to said subject a compound capable of modulating the activity of $LPA_3$ pathway. In another embodiment, the invention provides the use of a compound capable of modulating the activity of $LPA_3$ pathway for the manufacture of a medicament for treating or preventing a disorder or a condition associated with an abnormal level of red blood cells in a subject. In yet another embodiment, the invention provides a pharmaceutical composition for treating or preventing a disorder or a condition associated with an abnormal level of red blood cells in a subject, comprising a compound capable of modulating the activity of $LPA_3$ pathway. The compound includes those defined above.

According to the invention, the term "administering to a subject" includes dispensing, delivering or applying a compound capable of modulating the activity of $LPA_3$ pathway in a pharmaceutical formulation to a subject by any suitable route for delivery of the compound to the desired location in the subject to contact the compound with a target member of the $LPA_3$ pathway. The term "preventing" relates to the reduction of the risk of developing the prevailing disease, whereas the term "treating" relates to the amelioration of the symptoms of the prevailing disease condition, deceleration of the course of disease.

The term "a disorder or a condition associated with an abnormal level of red blood cells in a subject" used in the context of the invention includes those associated with a decrease or an increase in number of red blood cells or quantity of hemoglobin in the blood relative to normal blood levels, such as those associated with anemia and erythroid hyperplasia.

Anemia often occurs in patients suffering from acute or chronic kidney disease, infections, inflammation, cancer, irradiation, toxic substances, diabetes and surgery. Thus, the disorders and conditions associated with anemia are intended to encompass all kinds of anemic conditions, including aplastic anemia and myelodysplastic syndromes; microcytic anemia, hypochromic anemia, sideroblastic anemia, autoimmune hemolytic anemia; bone marrow transplantation; Churg-Strauss syndrome; Diamond Blackfan anemia; Fanconi's anemia; Felty syndrome; graft versus host disease; hematopoietic stem cell transplantation; hemolytic uremic syndrome; myelodysplasic syndrome; nocturnal paroxysmal hemoglobinuria; osteomyelofibrosis; pancytopenia; pure red-cell aplasia; purpura Schoenlein-Henoch; sideroblastic anemia; refractory anemia with excess of blasts; Shwachman syndrome; sickle cell disease; thalassemia major, thalassemia minor; and thrombocytopenic purpura. Anemia may cause serious symptoms, including hypoxia, chronic fatigue, lack of concentration, pale skin, low blood pressure, dizziness and heart failure.

The disorders or conditions associated with an abnormal level of red blood cells may also include erythroid hyperplasia, polycythemia vera and myelodysplastic syndrome, which may in turn cause itching, peptic ulcer disease, erythromelalgia, thrombotic complication, headaches, lack of concentration and fatigue.

As shown in the Examples below, LPA induction of erythropoiesis may depend on the presence of EPO. Therefore, in some preferred embodiments, the term "a disorder or a condition associated with an abnormal level of red blood cells in a subject" includes those that would benefit from EPO treatment. In a particularly preferred embodiment, the compound capable of modulating the activity of $LPA_3$ pathway according to the invention is administered or formulated with EPO.

An effective dose of the compound capable of modulating the activity of $LPA_3$ pathway according to the invention is used, in addition to physiologically acceptable carriers, diluents, adjuvants and/or excipient(s) for producing a pharmaceutical composition. The compound may conveniently be formulated in unit dosage form by conventional pharmaceutical techniques. Such techniques include the step of bringing into association the compound and the physiologically acceptable carriers, diluents, adjuvants and/or excipient(s). In general, the formulations are prepared by uniformly and intimately bringing into association the compound with liquid carriers or finely divided solid carriers or both, and then, if necessary, shaping the product. In the case of using a $LPA_3$-mediating compound, the dose thereof can vary depending on the route of administration, the age and weight of the subject to be treated, the nature and severity of the diseases to be treated and similar factors. The dose, when administered to a subject, such as cells or a human subject, is sufficient to produce a selected effect. For example, the amount of the $LPA_3$-mediating compound to be administered is an amount that leads to a physiologically meaningful increase or decrease in the receptor activity of $LPA_3$. Normally, the daily dose ranges between 0.1-500 mg/kg body weight, preferably 0.1-100 mg/kg body weight, more preferably 0.1-10 mg/kg body weight, and most preferably 0.1-1.0 mg/kg body weight, which can be formulated as a single dose to be administered once per day, or be subdivided into two or more daily doses.

Suitable administration forms include, but are not limited to, topical, oral, rectal, intraperitoneal or parenteral (e.g., intravenous, subcutaneous or intramuscular) preparations. Preferred are oral and parenteral preparations. The customary galenic preparation forms, such as tablets, sugar-coated tablets, capsules, dispersible powders, granulates, aqueous solutions, alcohol-containing aqueous solutions, aqueous or oily suspensions, syrups, juices or drops, may also be used.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavourings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators.

Examples of such additives are tartrate and citrate buffers, ethanol and sequestering agents (such as ethylenediaminetetraacetic acid and its non-toxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats, and solid high molecular weight polymers, such as polyethylene glycol.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

As indicated above, the compound capable of modulating the activity of $LPA_3$ pathway, such as the $LPA_3$-mediating compound, may be administered as a combination therapy with further active agents, such as EPO, useful in the treatment of anemia and associated disorders and conditions. The suitable doses of these active agents are known by those skilled in the art. In the case of EPO, however, since LPA is shown below to work with EPO to enhance erythropoiesis in a synergistic manner, the mount of EPO used in a daily dose can be significantly reduced according to the invention, whereby the adverse side effects and the economic burden caused by long-term administration of EPO are diminished. The amount of EPO administered to the human or animal is normally from 10 to 1,500 U/kg body weight per daily dose.

For a combination therapy, the active ingredients may be formulated as compositions containing several active ingredients in a single dose form and/or as kits containing individual active ingredients in separate dose forms. The active ingredients used in combination therapy may be co-administered or administered separately.

The following examples are given for the purpose of illustration only and are not intended to limit the scope of the invention.

Example 1

Materials and Methods

Zebrafish Maintenance and Embryo Collection

Wild-type zebrafish (*Danio rerio*) obtained from the Zebrafish Information Research Center (Eugene, Oreg., USA) were inbred at 27-28° C. Embryos were collected from natural spawning, washed, and incubated in 0.3× Danieau's buffer at 28° C. until being used. Each stage of fish embryos was determined from their morphology. Embryos at 12 hour post-fertilization (hpf) were treated with 0.2 mM 1-phenyl-2-thiourea (PTU) (Sigma, St. Louis, Mo., USA) in 0.3× Danieau's buffer to suppress melanization. Dechorionation of embryos was carried out with 0.01 g/ml protease (Sigma).

Morpholino Antisense Oligonucleotides

Glass capillary tubes were pulled by a horizontal puller (P-97, Sutter Instrument, Navato, Calif., USA). Two $zLPA_3$ translation-blocking (t)MOs (Gene Tools, Philomath, Oreg., USA) were utilized as follows:

tMO1: 5'-CACTGTCCTAGTGGGTTTTGTCCAA-3' (−27 to −3) (SEQ ID No. 1); and tMO2: 5'-ATGGCCAGGCACAACATCTGCTA-3' (+1 to +23) (SEQ ID No. 2).

The MOs were prepared at 1 mM in sterile $H_2O$ as a stock solution, and further diluted into desired working concentrations in 1× Danieau's buffer with 0.5% phenol red. Fish embryos were fixed on 1% injection agar plates, and 2.3 nl of solution was injected into the yolk sac and blastodisc interface with a nanoliter injector (World Precision Instruments, Sarasota, Fla., USA). The injected embryos were incubated in 0.3× Danieau's buffer at 28.5° C. for further experiments.

O-Dianisidine Blood Cell Staining

Embryos from designated stages were incubated in freshly prepared o-dianisidine solution (40% ethanol, 0.01 M sodium acetate, 0.65% $H_2O_2$, and 0.6 mg/ml o-dianisidine [Sigma]) for 15 minutes in the dark. Embryos were observed under a stereomicroscope, and embryos that exhibited o-dianisidine staining in red were considered have red blood cells.

Cultures of Hematopoietic Stem Cells $CD133^+$ stem cells were isolated from human umbilical cord blood by magnetic microbead selection using Direct CD34 progenitor isolation beads (Miltenyi Biotech, Bergisch Gladbach, Germany) and MACS LS-columns (Miltenyi Biotech), and were subsequently cultured. In stage I, $10^5$ $CD133^+$ cells were cultured in 10 ml of EDM ($10^4$ cells/ml), containing human stem cell factor (SCF, 50 ng/ml), human EPO (6 IU/ml), human interleukin (IL)-3 (10 ng/ml), human vascular endothelial growth factor (VEGF, 10 ng/ml), and human insulin-like growth factor (IGF)-II (250 ng/ml) for 6 days. In stage II, cells were cultured in 10 ml of EDM ($3 \times 10^4$ cells/ml) in the presence of SCF (50 ng/ml) and EPO (6 IU/ml) for 4 days. In stage III, cells were cultured in 10 ml of EDM ($5 \times 10^4$ cells/ml) in the presence of SCF (50 ng/ml) and EPO (2 IU/ml) for 6 days. Cultured cells respectively underwent 30-, 20-, and 10-fold expansions in stages I, II, and III. All cell cultures were incubated at 37° C. in 5% $CO_2$ under humidified conditions. LPA (Sigma) was prepared in chloroform and methanol (1:9) and stored at −20° C. LPA was added to serum-free medium with 0.005% fatty acid-free BSA as a carrier.

Treatment with Ki16425 and Quercetin

Ki16425 (Cayman Chemical, Ann Arbor, Mich., USA) powder was diluted in dimethyl sulfoxide (DMSO) at a concentration of 40 mM as the stock. At the ends of stages I and II, HSCs were pretreated with Ki16425 in serum-free medium for 1 h. Then, cells were cultured in media of stages II and III containing Ki16425 at a final concentration of 20 μM. Quercetin (Sigma) was dissolved in DMSO at 100 mM as the stock and stored at −20° C. Quercetin was diluted into each final concentration by culture media for treatment.

Short-Hairpin (sh)RNA Nucleofection

Around $5 \times 10^5$ HSCs at the ends of stages I and II were prepared for transfection. The shRNA plasmid against $LPA_1$ and $LPA_3$ was transiently transfected into HSCs using AMAXA® NUCLEOFECTION®. (Lonza, Cologne, Germany) according to the manufacturer's protocol for $CD34^+$ stem cells (www.lonzabio.com). Each target plasmid was constructed with a green fluorescent protein (GFP) gene to confirm that the transfection efficiency was >70%. After 48 h, GFP-positive cells were sorted out by BD FACSAria II Cell Sorter (BD Bioscience, San Diego, Calif., USA) and cultured in media for further stages.

mRNA Expression

Total RNA extraction was isolated using Trizol Reagent (Invitrogen, Carlsbad, Calif., USA). Complementary (c)DNA was synthesized from 1 μg total RNA with a reverse-transcription polymerase chain reaction (RT-PCR). Primer sequences were:

```
GATA-1
                                       (SEQ ID No. 3)
5'-CAAGAAGCGCCTGATTGTCAG-3' (forward)
and (SEQ ID No. 4)
5'-AGTGTCGTGGTGGTCGTCTG-3' (reverse);

LPA1
                                       (SEQ ID No. 5)
5'-TGTCTCGGCATAGTTCTGGACCC-3' (forward)
and (SEQ ID No. 6)
5'-CATTTCTTTGTCGCGGTAGGAG-3' (reverse);

LPA3
                                       (SEQ ID No. 7)
5'-TGACTGTCTTAGGGGCGTTT-3' (forward)
and (SEQ ID No. 8)
5'-TTCTCCTGAGAGAAGCAGCA-3' (reverse);

CD71
                                       (SEQ ID No. 9)
5'-GGATAAAGCGGTTCTTGGTACC A-3' (forward)
and (SEQ ID No. 10)
5'-CCAGTAACCGGATGCTTCACA-3' (reverse);
and GlyA
                                       (SEQ ID No. 11)
5'-ACAGACAAAT GATACGCACAAACGGG-3' (forward)
and (SEQ ID No. 12)
5'-GGGCTTTTCTTTATCAGTCGGCGA-3' (reverse).
```

A real-time PCR with the mixture reagent SYBR®-Green I (Thermo Scientific, San Diego, Calif., USA) was carried out on an iCycler iQ™ real-time detection system (Bio-Rad, Hercules, Calif., USA). The specificity of the primers was confirmed from a single peak of the melting curve. Each target mRNA level was evaluated from the real-time threshold cycle and compared to the GAPDH amount as an internal control.

Immunofluorescence Analysis

Harvested cells were fixed on cover slides in phosphate-buffered saline (PBS) containing 4% formaldehyde for 10 minutes, and permeated through both the plasma and nuclear membrane by 0.02% TRITON X-100™ for 10 minutes. After blocking with 5% bovine serum albumin (BSA) for 1 hour, samples were incubated with mouse immunoglobulin (IgG) or anti-β-catenin primary antibody (BD Bioscience) overnight. Finally, cells were stained with 4,6-diamidino-2-phenylindole (DAPI, Sigma) for 5 minutes and a goat anti-mouse IgG FITC secondary antibody for 1 hour. Slides were mounted with FLUOROMOUNT-GT™ (Emsdiasum, Fort Washington, Pa., USA) and visualized using a DeltaVision OMX Core fluorescence microscope (Applied Precision, Issaquah, Wash., USA).

Flow Cytometry

HSC cultures were collected, washed, and stained either with anti-GlyA-PE and anti-CD71-PE/Cy5 for 30 minutes (BD Biosciences Pharmingen, San Diego, Calif., USA). Stained cells were washed and resuspended in PBS. Non-stained and single-stained samples were prepared for fluorescent compensation. For all experiments, analysis of cells used a FACSCalibur instrument (BD Biosciences) and FCS Express software (De Novo, Los Angeles, Calif., USA).

Statistical Analysis

Experiments were assessed using Excel computer software. Differences between groups were assessed using a non-parametric analysis of variance (ANOVA). p values of <0.05 were considered significant.

Example 2 zLPA$_3$ tMO Affects Red Blood Cell Formation in Zebrafish

Figure 1:
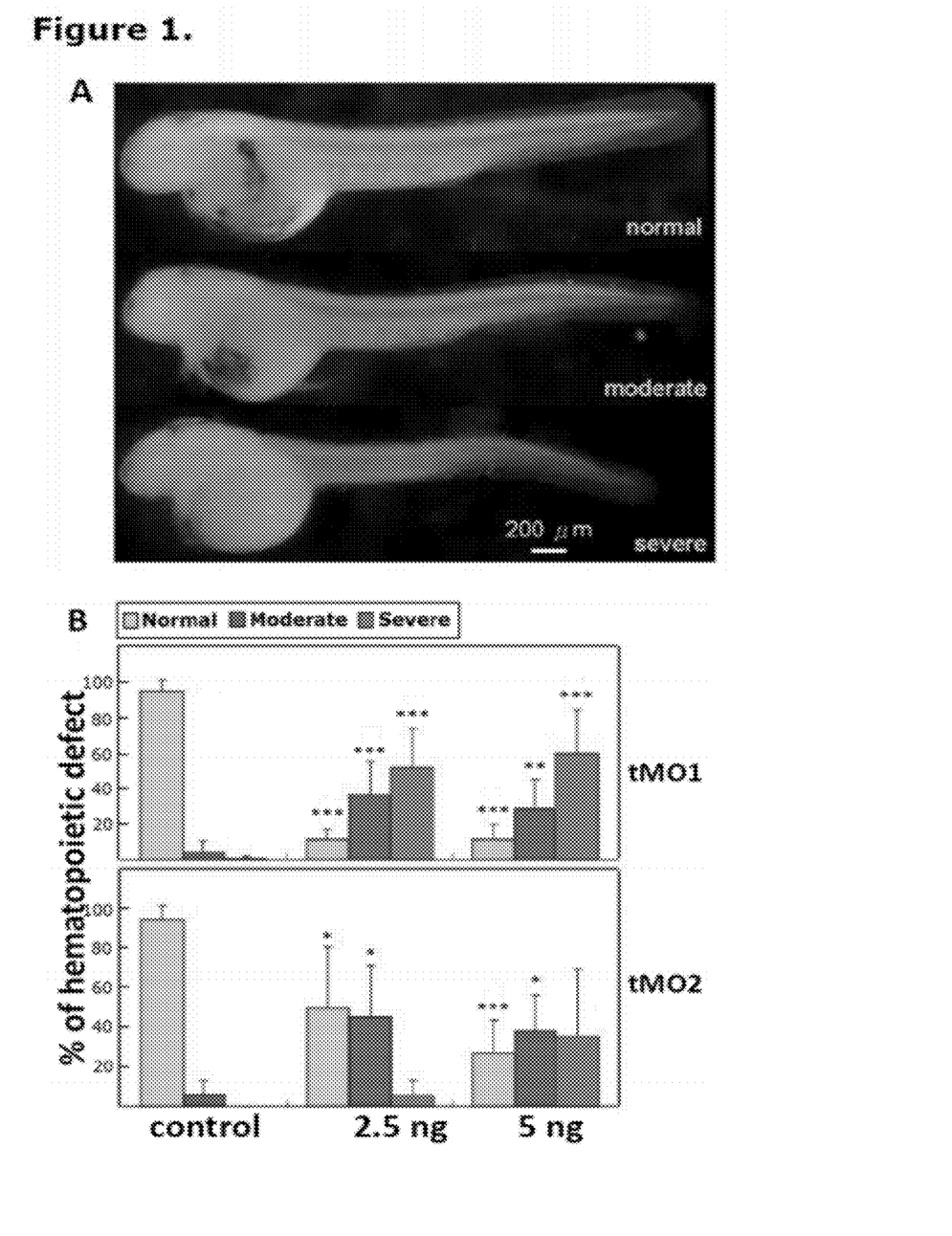

To investigate the effects of zLPA$_3$, two translational-blocking MOs, tMO1 and tMO2, were synthesized and injected into one-cell-stage zebrafish embryos. The specificity, potency, and efficacy of tMO1 and tMO2 in blocking zLPA$_3$ translation were confirmed. By o-dianisidine staining, which is a general indicator of hemoglobin in erythrocytes, we found that LPA$_3$ knockdown caused erythropoietic defects. O-Dianisidine staining was significant in control embryos, but had decreased in LPA$_3$ knockdown embryos. The degrees of erythrocyte formation were classified into normal, moderate, and severe as shown at 48 hpf. A dose-dependent effect of LPA$_3$ knockdown was observed in both zLPA$_3$ tMO1 and tMO2 embryos at 0, 2.5, and 5 ng (FIG. 1). In addition, we collected embryos from 60 hpf, and the defective patterns were similar to those of the 48-h-treatment groups (see supplementary data). The percentages of erythrocyte-defective embryos were significantly higher in zLPA$_3$ tMO1- and tMO2-treated groups compared to control embryos.

Example 3

In Vitro Hematopoiesis Using Human CD133$^+$ Stem Cells

Figure 2:
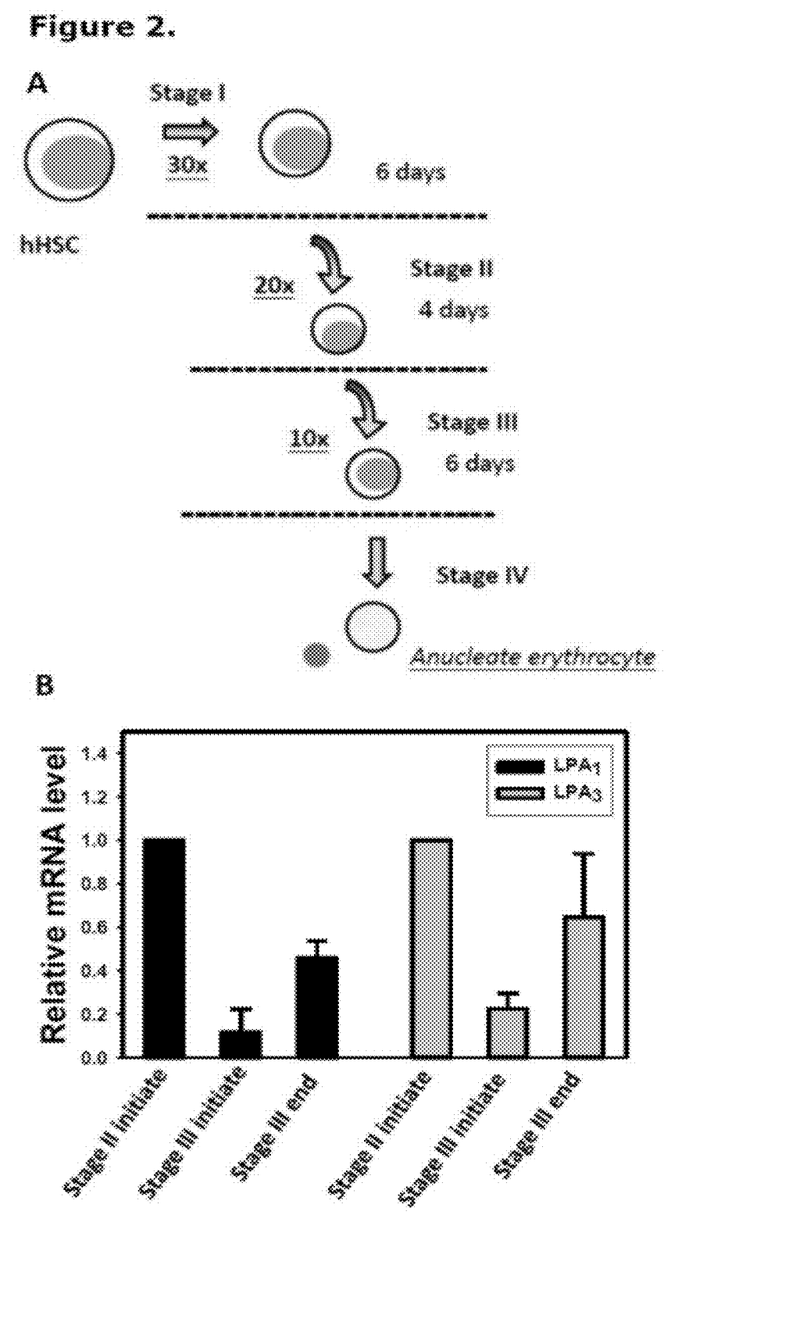

To confirm the observation that LPA$_3$ may be involved in regulating hematopoiesis, we established an erythropoiesis system using cord-blood-derived hHSCs as described above (FIG. 2A). In these procedures, human CD133$^+$ stem cells were induced by growth factors to change into mature erythrocytes. hHSCs underwent both proliferation and differentiation in four stages (FIG. 2A). In stage I, hHSCs expanded by around 30-fold into myeloid progenitors. Sequentially, progenitor cells were induced to go through erythropoietic differentiation by SCF and EPO treatments during stages II and III. Progenitor cells respectively further expanded by 20- and 10-fold, and generated a greater number of erythroid cells expressing specific biomarkers: CD71 and GlyA. In stage IV, erythroblasts were stimulated to enucleate and become mature erythrocytes. The expression patterns of LPA$_1$ and LPA$_3$ during different stages were determined by a real-time PCR. The mRNAs of LPA$_1$ and LPA$_3$ were detected in both stages II and III. In contrast, expression levels of LPA$_1$ and LPA$_3$ were higher at the end of stage I, and decreased as cells entered stages II and III (FIG. 2B).

Example 4

LPA Receptor Antagonist Blocks Erythropoietic Processes

To investigate the roles of LPA$_1$ and LPA$_3$ in erythropoietic differentiation, we used Ki16425, an LPA$_1$- and LPA$_3$-specific antagonist, to block receptor-activated signaling processes. Cells harvested from the end of stage I were incubated in serum-free media with DMSO or Ki16425 for 1 hour, and allowed to continue into stage II differentiation. In stage II, the expansion of erythroblasts was significantly lower under Ki16425 treatment compared to the control group (data not shown). In addition, relative mRNA levels of CD71 and GlyA both decreased with Ki16425 treatment (FIG. 3A). The long-term effects of LPA$_1$ and LPA$_3$ inhibition with Ki16425 treatment were also monitored. hHSCs were treated with Ki16425 in stage II, III, or both stages. Treated cells were harvested and analyzed after 10 days. mRNA expression levels of CD71 and GlyA were affected under constant Ki16425 treatment (FIG. 3A). Ki16425 treatment in stage II only caused greater inhibition than in stage III, especially in terms of GlyA mRNA levels. Furthermore, Ki16425's effects on CD71 and GlyA protein levels were also monitored by flow cytometry. In stage III, high percentages of cells exhibiting surface CD71 and GlyA were observed after EPO treatment. However, with Ki16425, suppression of the expression of these two markers was observed. More than half of Ki16425-treated cells were trapped in an undifferentiated stage (CD71$^-$ GlyA$^-$ population). Our data indicated that blocking LPA$_1$ and LPA$_3$ signaling inhibited the differentiation of erythrocytes.

Example 5

LPA Receptor Knockdown Prevents Erythropoietic Processes

Since Ki16425 blocks both LPA$_1$ and LPA$_3$, we further attempted to clarify which receptor is responsible for regulating erythropoiesis. Plasmids containing LPA$_1$ and LPA$_3$ shRNA or a scrambled sequence were transfected into hHSCs by electrical nucleofection procedures. After 24 hours, GFP-positive cells were isolated for further studies. The knockdown efficacies of LPA$_1$ and LPA$_3$ were individually determined (FIG. 4A). Messenger RNA levels of CD71 and GlyA were lower in LPA$_3$-knockdown cells in stages II and III, compared to control and LPA$_1$-knockdown cells (FIG. 4B). Similar results were observed for protein levels. LPA$_3$-knockdown cells had the lowest percentage of CD71$^+$ and GlyA$^+$ double-positive erythroblasts, whereas LPA$_1$-knockdown cells showed similar patterns as the control (FIG. 4C). We concluded that the LPA-regulated erythropoiesis is mainly mediated through activating LPA$_3$. The results further suggested that the specific blockage of LPA$_3$ signaling inhibits the erythropoietic process.

Example 6

Exogenously Added LPA Enhances Erythrocyte Differentiation

Figure 5:
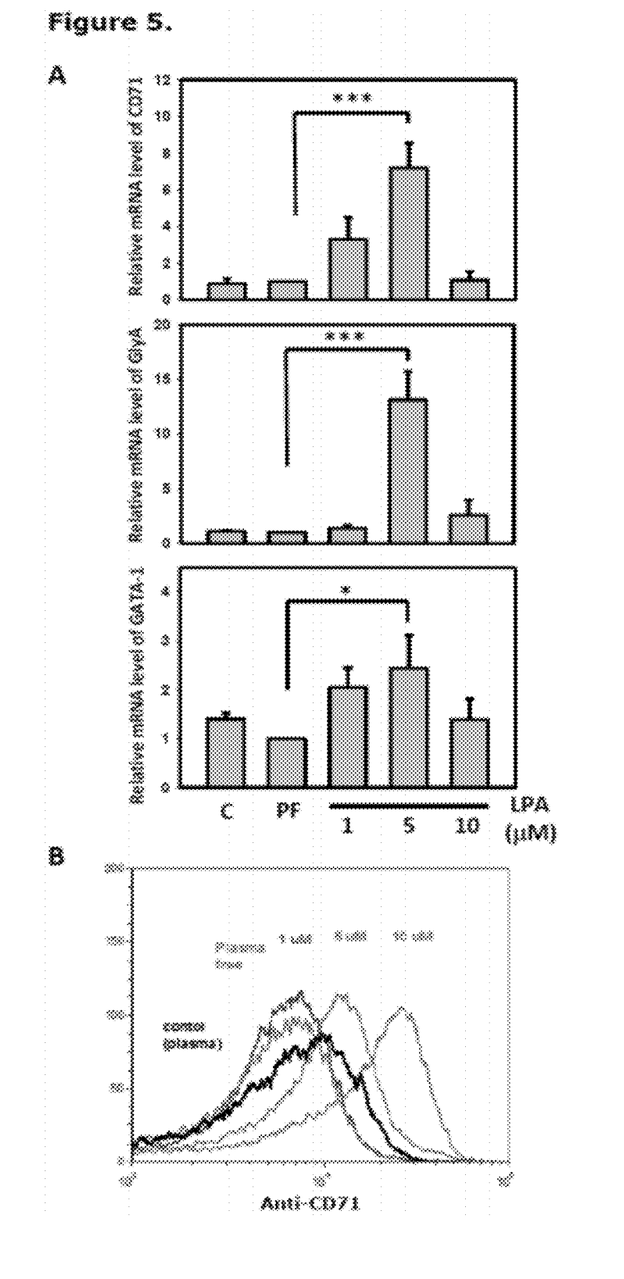

The direct effects of LPA on the development of hHSCs are further determined. A culture of cord blood progenitor cells was established in plasma-free medium to exclude the effect of endogenous serum-derived LPA. These cells were then cultured in the absence or presence of LPA 18:1 (1~10 µM) for 24 hours. Short-term culture under plasma-free conditions showed no obvious differences from the control. However, long-term plasma-free cultured cells had a lower survival rate and were poorly differentiated (data not shown). In stage II, 24-hour LPA treatment elevated mRNA levels of CD71, GlyA, and GATA-1 in concentration-dependent manners (FIG. 5A). At the end of stage II induction, protein expression levels were analyzed at 4 days using anti-CD71 PE.Cy5 and anti-GlyA PE. Cells treated with 5 and 10 µM LPA expressed higher levels of CD71, but not GlyA (FIG. 5 B). However, the differentiation of erythroid cells severely decreased in the absence of EPO, even in the presence of LPA (data not shown). These results suggest that LPA enhances the EPO-dependent erythropoietic process.

Example 7

Figure 6:
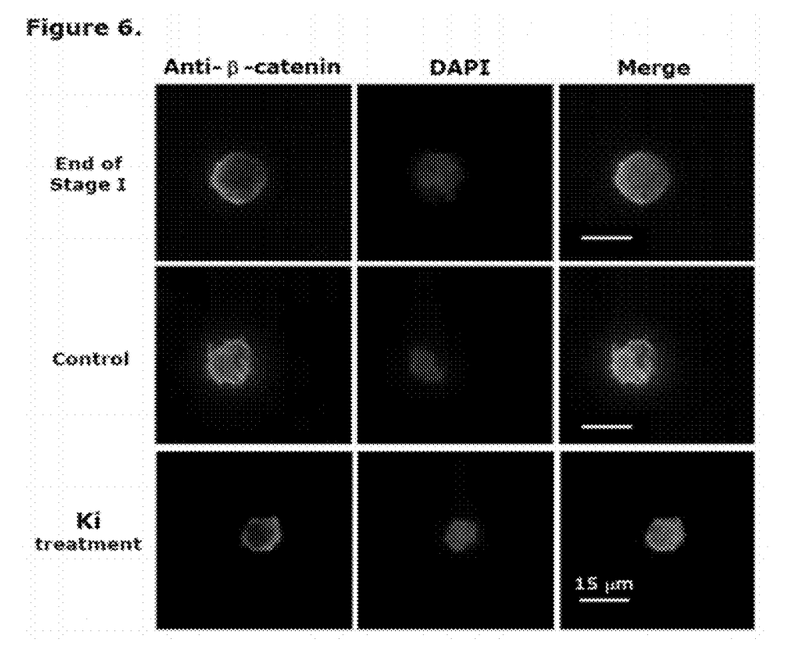
FIG. 6 is a diagram demonstrating the translocation of β-catenin in hHSCs with/without Ki treatment for 24 hours in stage II.

V-Catenin Regulates the Early Stage of Erythropoiesis

β-Catenin translocation is known as a downstream signaling process activated by LPA receptors in cancer cells. hHSCs are cultured in the absence and presence of Ki16425 for 24 hours and then stained cells with an anti-β-catenin antibody and DAPI. Translocation of β-catenin into nuclei was obvious in early erythroid cells, while this was inhibited by Ki16425 (FIG. 6). The results suggest that the β-catenin/TCF pathway is involved in the early stage of hematopoietic differentiation, and inhibition by Ki16425 may occur through suppressing β-catenin translocation.

To clarify the role of β-catenin in erythropoiesis, quercetin, an inhibitor of the β-catenin/TCF pathway, was used to treat HSCs in the early stage. Because CD71's function is essential for iron transport in early erythroid cells, we focused on CD71 expression. The increase in CD71 mRNA under LPA induction was suppressed by quercetin at different concentrations of 5, 20, and 50 µM, and similar pattern was also observed in the GATA-1 mRNA level (FIG. 7A). The protein expression of CD71 was detected by flow cytometry, and the induction of LPA decreased under quercetin treatment (FIG. 7B). In addition, our results also demonstrated that Ki16425 treatment suppressed LPA enhancements for erythropoiesis (FIG. 7A).

Figure 3:
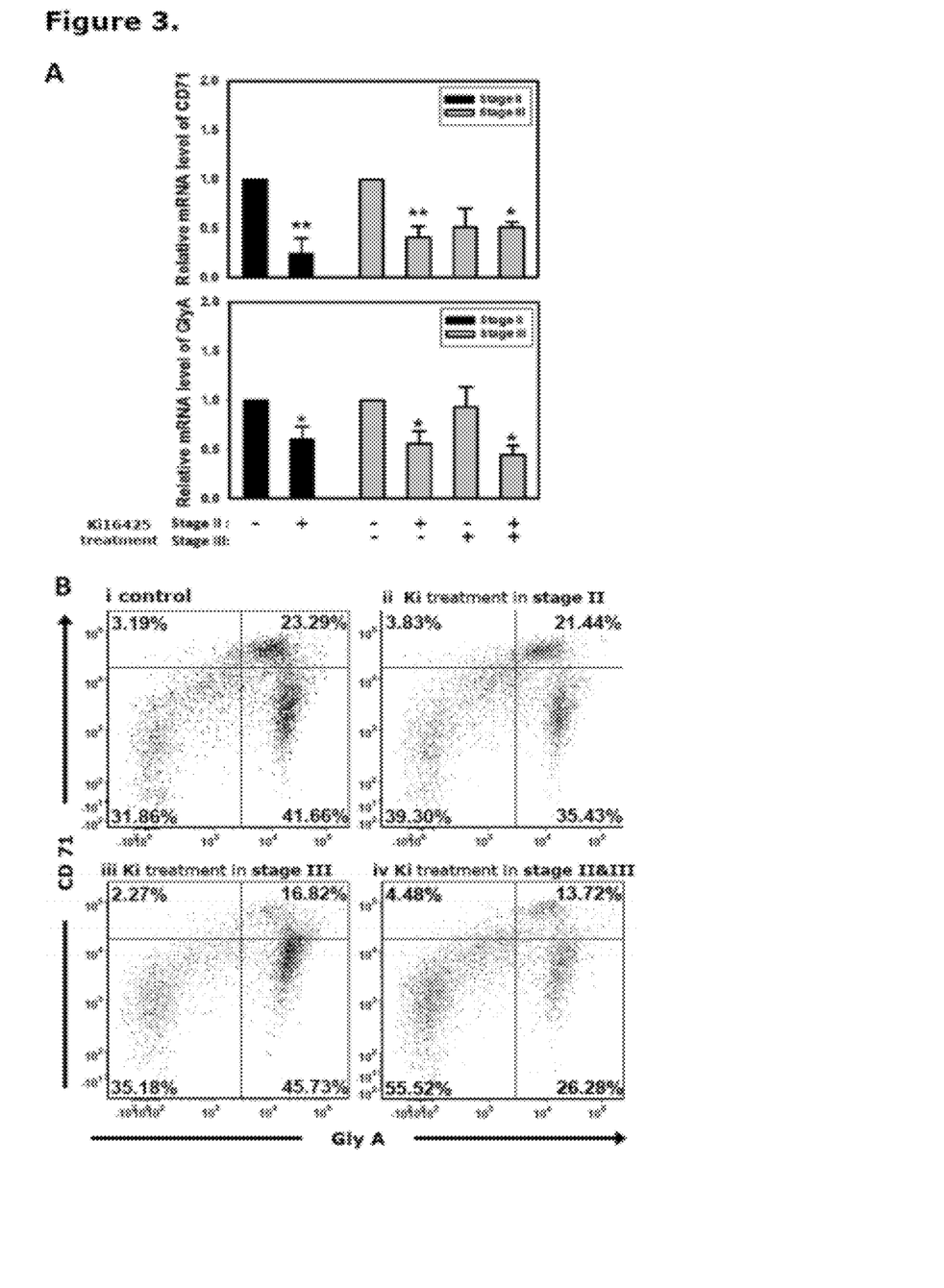
Figure 4:
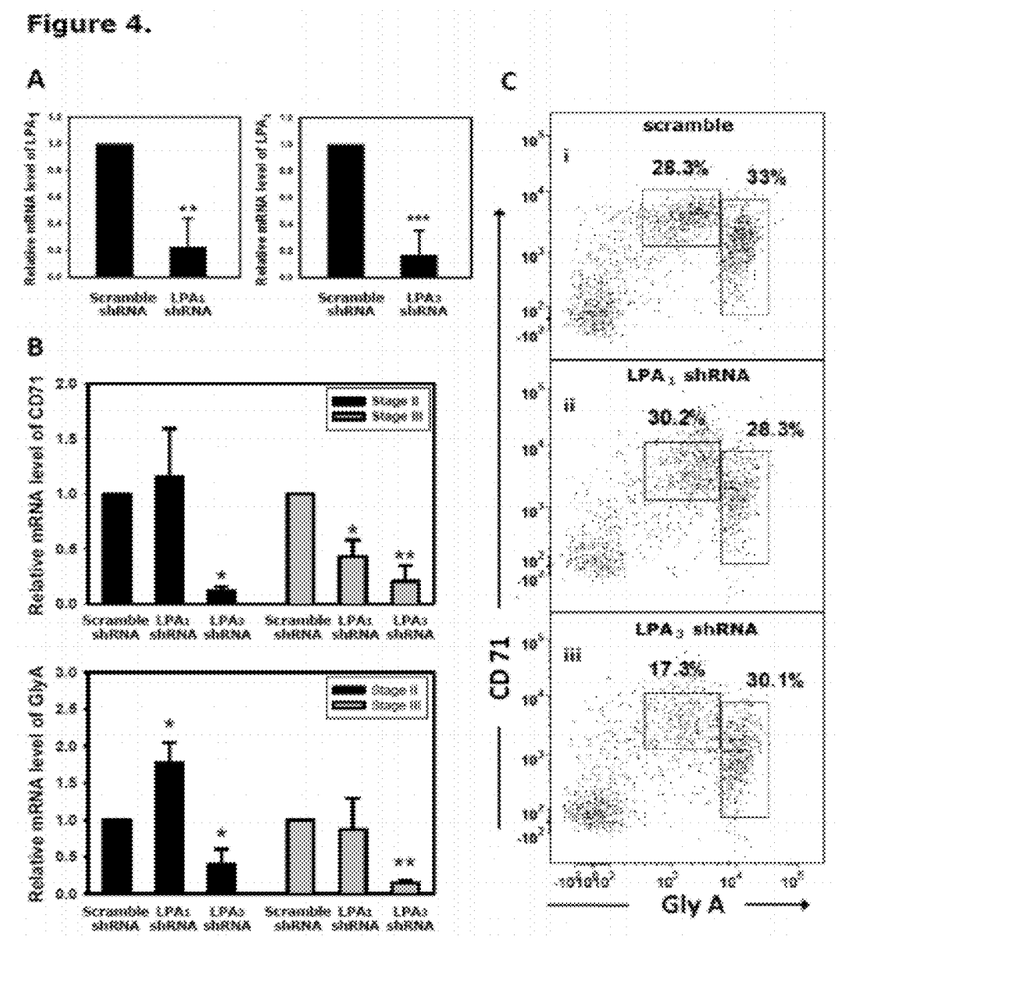

The experimental data above indicate that the regulatory roles of LPA in erythropoietic processes via activation of LPA$_3$. In vivo, LPA$_3$-knockdown zebrafish embryos showed erythropoiesis defects (FIG. 1). Subsequently, an hHSC erythropoietic system was adopted to confirm that the erythroid differentiation process was affected by blocking of LPA$_3$ signaling (FIGS. 3, 4). Under physiological conditions, LPA is constitutively present in human plasma at concentrations at 1~15 µM. Under long-term culture conditions without human plasma, the survival rate of hHSCs was significantly decreased (data not shown). This result suggested that LPA may play a critical role in both the survival of HSCs and their differentiation into mature erythrocytes. Exogenously added LPA induced the expression of CD71 and GlyA, which are surface markers of erythrocytes. Expression levels of GATA-1, one of the essential mediators of the EPO receptor (EPOR) that affects and promotes erythroid maturation, were also enhanced by LPA treatment (FIG. 5). These results strongly suggested that LPA acts synergistically with EPO to enhance erythropoietic processes.

Figure 7:
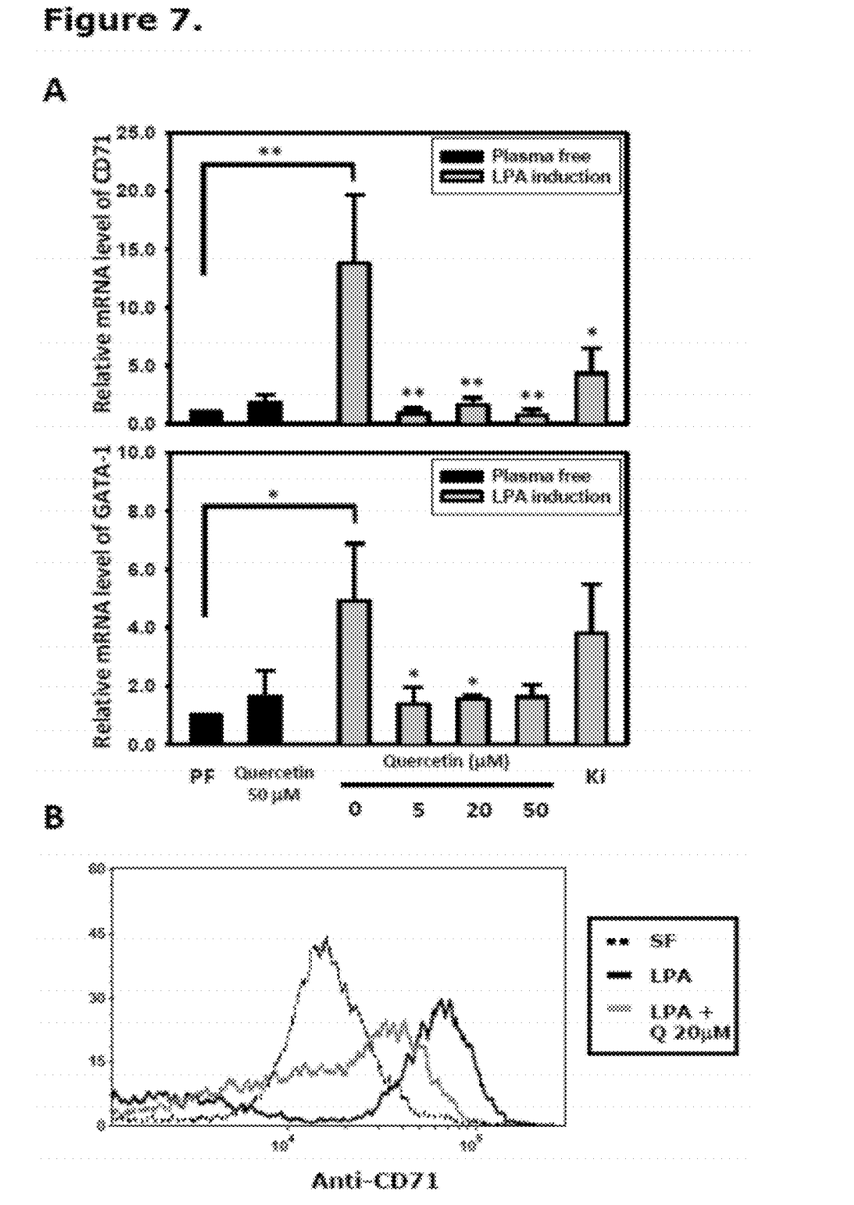

Wnt/β-catenin signaling was suggested to be critical to the survival and development of HSCs. In stem cells, Wnt signaling pathways have diverse functions. Wnt10b has an inhibitory effect on BFU-E differentiation. In contrast, Wnt5a and Wnt2b act as activators of this process. β-Catenin is a crucial factor in maintaining murine embryonic stem cells in an undifferentiated status. Activation of β-catenin promotes the growth of HSCs in vitro and maintains the self-renewal of HSCs under long-term culture. In *Xenopus* embryos, Wnt4/β-catenin expressed in the mesoderm of the ventral blood island is essential for the expression of hematopoietic and erythroid marker genes. In addition, constitutive β-catenin activation caused defects of HSCs and blocked multilineage differentiation in mouse blood cells. In contrast, another report suggested that inactivation of the β-catenin gene is dispensable for hematopoiesis and lymphopoiesis in bone-marrow progenitors. Furthermore, the β-catenin pathway is activated by G protein-coupled LPA receptors which affect several cellular functions. In our current study, we confirmed that activation of LPAR induced β-catenin activation at an early stage of erythropoiesis (FIG. 6). In addition, the hematopoiesis enhanced by LPA was blocked by inhibition of the β-catenin/TCF pathway (FIG. 7). These results suggest roles for LPARs and β-catenin in hHSC-derived erythropoiesis. Translocation of β-catenin may be important for stem cell differentiation.

It is known that EPO is the main regulator of erythropoietic processes, and the EpoR is primarily expressed in hematopoietic progenitor cells. Upon EPO binding, dimerization of EpoR activates the JAK/STAT signaling pathway to modulate erythropoiesis. In addition, the GATA-1 transcription factor is also essential for normal erythroid cell development. DNA binding and transactivation of GATA-1 are required for both primitive and definitive stages of hematopoiesis in zebrafish. Activation of the EPOR phosphorylates GATA-1 and regulates its activity via the PI3-kinase/AKT signaling pathway in primary fetal liver erythroid progenitors and cultured erythroid cells. GATA-1 transactivates the gene expression of the EPOR and GATA-1 itself. The interaction between the EPOR and GATA-1 is responsible for the stability of erythropoiesis. The results (FIG. 5) showed that LPA enhanced the expression of the erythroid biomarkers, CD71 and GlyA, during erythroid differentiation. In addition, GATA-1 gene expression also increased under LPA treatment. These results demonstrated an enhancing effect of LPA on maturation of erythroid cells in our system. The inventors also tried to culture hHSCs in an EPO-free condition. However, even in the presence of LPA in culture, the differentiation of erythroid cells was severely hampered (data not shown). These results suggest that LPA induction of erythropoiesis may depend on the presence of EPO, which activates the transcription factor, GATA-1, to trigger expression of other essential protein(s) for erythroid differentiation.

While the invention has been described with reference to the preferred embodiments above, it should be recognized that the preferred embodiments are given for the purpose of illustration only and are not intended to limit the scope of the present invention and that various modifications and changes, which will be apparent to those skilled in the relevant art, may be made without departing from the spirit and scope of the invention.

All papers, publications, literature, patents, patent applications, websites, and other printed or electronic documents referred herein, including but not limited to the references listed below, are incorporated by reference in their entirety. In case of conflict, the present description, including definitions, will prevail.

What is claimed is:

1. A method for modulating erythropoietin-dependent erythropoiesis via Lysophosphatidic acid receptor subtype 3 (LPA$_3$) in a subject comprising administering to said subject a compound capable of mediating Lysophosphatidic acid receptor subtype 3 (LPA$_3$) wherein the compound is selected from the group consisting of LPA, 2-arachidonoyl-LPA, sphingosine 1-phosphate (S1P), lysophosphatidyl choline (LPC), sphingosylphosphorylcholine, 1-oleoyl-2-O-methyl-rac-glycerophosphothionate (OMPT), (3S)-1-fluoro-3-hydroxy-4-butyl-1-phosphonate (XY-17), T13, T10, VPC12086, VPC31143, mono-fluorinated LPA, 3-[({4-[4-({[1-(2-chloro-4-methylphenyl)ethoxy]carbonyl}amino)-3-methyl-1,2-oxazol-5-yl]phenyl}methyl)sulfanyl]propanoic acid (Ki16425), diacylglycerol pyrophosphate (DGPP), VPC12249, dioctyl-PA, 1-O-acyl-α-fluoromethylenephosphonate, α-hydroxymethylenephosphonate LPA, and pharmaceutically acceptable salts thereof.

2. The method of claim 1, wherein the compound is capable of enhancing the activity of LPA$_3$.

3. The method of claim 1, wherein the subject is selected from the group consisting of human and non-human animal.

4. The method of claim 1, wherein the subject is a biological sample selected from the group consisting of a cell, a tissue, or an organ that is isolated from an organism in which red blood cells are utilized as principal means for delivering oxygen.

5. The method of claim 1, further comprising administering erythropoietin to the subject.

6. The method of claim 1, wherein the compound is LPA, 1-oleoyl-2-0-methyl-rac-glycerophosphothionate (OMPT), or 3-[({4-[4-({[1-(2-chloro-4-methylphenyl)ethoxy]carbonyl}amino)-3-methyl-1,2-oxazol-5-yl]phenyl}methyl)sulfanyl]propanoic acid (Ki16425).

7. The method of claim 5, wherein the subject is cultured human hematopoietic cells.

8. A method of enhancing erythropoietin-dependent erythropoiesis in hematopoietic cells, comprising contacting Lysophosphatidic acid (LPA), 1-oleoyl-2-0-methyl-rac-glycerophosphothionate (OMPT), or 3-[({4-[4-({[1-(2-chloro-4-methylphenyl)ethoxy]carbonyl}amino)-3-methyl-1,2-oxazol-5-yl]phenyl}methyl)sulfanyl]propanoic acid (Ki16425) with Lysophosphatidic acid receptor subtype 3 (LPA$_3$) on the hematopoietic cells.

9. The method of claim 8, further comprising a step of administering erythropoietin to the hematopoietic cells.

10. The method of claim 9, wherein the hematopoietic cells are cultured human hematopoietic cells.

11. The method of claim 1, wherein the subject has a disorder or a condition associated with an abnormal level of red blood cells.

12. The method of claim 11, wherein the compound is Lysophosphatidic acid (LPA), 1-oleoyl-2-0-methyl-rac-glycerophosphothionate (OMPT), or 3-[({4-[4-({[1-(2-chloro-4-methylphenyl)ethoxy]carbonyl}amino)-3-methyl-1,2-oxazol-5-yl]phenyl}methyl)sulfanyl]propanoic acid (Ki16425).

13. The method of claim 12, wherein the compound is 1-oleoyl-2-O-methyl-rac-glycerophosphothionate (OMPT).

* * * * *

SEQUENCE LISTING

```
<160> NUMBER OF SEQ ID NOS: 12

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cactgtccta gtgggttttg tccaa                                            25

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atggccaggc acaacatctg cta                                              23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 3
caagaagcgc ctgattgtca g                                    21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agtgtcgtgg tggtcgtctg                                      20

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtctcggca tagttctgga ccc                                  23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
catttctttg tcgcggtagg ag                                   22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgactgtctt aggggcgttt                                      20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttctcctgag agaagcagca                                      20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

-continued

```
ggataaagcg gttcttggta cca                                          23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccagtaaccg gatgcttcac a                                            21

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acagacaaat gatacgcaca aacggg                                       26

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12 gggctttttct ttatcagtcg gcga                                        24
```